(12) United States Patent
Fogarty (10) Patent No.: US 8,801,594 B2
(45) Date of Patent: Aug. 12, 2014

(54) FLUID CONTROL SYSTEM FOR INFLATABLE SPHINCTER PROSTHESES

(71) Applicant: Terence M. Fogarty, Hudson, WI (US)

(72) Inventor: Terence M. Fogarty, Hudson, WI (US)

( * ) Notice: Subject to any disclaimer, the term of this patent is extended or adjusted under 35 U.S.C. 154(b) by 0 days.

(21) Appl. No.: 13/800,125

(22) Filed: Mar. 13, 2013

(65) Prior Publication Data
US 2013/0303841 A1 Nov. 14, 2013

Related U.S. Application Data

(60) Provisional application No. 61/644,408, filed on May 8, 2012.

(51) Int. Cl.
*A61F 2/02* (2006.01)
*A61F 2/00* (2006.01)

(52) U.S. Cl.
CPC .................................. *A61F 2/004* (2013.01); *Y10S 128/25* (2013.01)
USPC .......................... 600/31; 600/29; 128/DIG. 25

(58) Field of Classification Search
USPC ......... 600/29–31, 32; 128/DIG. 25; 606/157; 623/14.13, 23.66–23.68
See application file for complete search history.

(56) References Cited

U.S. PATENT DOCUMENTS

| | | |
|---|---|---|
| 3,744,063 A | 7/1973 | McWhorter et al. |
| 3,750,194 A | 8/1973 | Summers |
| 3,863,622 A | 2/1975 | Buuck |
| 3,903,894 A | 9/1975 | Rosen et al. |
| 4,167,952 A | 9/1979 | Reinicke |
| 4,197,835 A | 4/1980 | Reinicke |
| 4,222,377 A | 9/1980 | Burton |
| 4,256,093 A | 3/1981 | Helms et al. |
| RE31,121 E | 1/1983 | Reinicke |
| 4,386,601 A | 6/1983 | Trick |
| 4,412,530 A | 11/1983 | Burton |
| 4,417,567 A | 11/1983 | Trick |
| 4,419,985 A | 12/1983 | Trick |
| 4,437,457 A | 3/1984 | Trick et al. |
| 4,682,583 A | 7/1987 | Burton et al. |
| 4,721,509 A | 1/1988 | Craggs |
| 4,878,889 A | 11/1989 | Polyak |
| 4,994,020 A | 2/1991 | Polyak |
| 5,478,305 A | 12/1995 | Craggs |
| 5,593,443 A | 1/1997 | Carter et al. |
| 5,724,994 A * | 3/1998 | Simon et al. .................. 128/885 |
| 5,893,826 A | 4/1999 | Salama |
| 7,011,622 B2 | 3/2006 | Kuyava et al. |
| 7,282,023 B2 | 10/2007 | Frering |
| 2007/0073099 A1 | 3/2007 | Forsell |
| 2007/0213580 A1 | 9/2007 | Schrag |
| 2007/0232848 A1 | 10/2007 | Forsell |
| 2010/0016652 A1 | 1/2010 | Bonni |
| 2010/0160716 A1 | 6/2010 | Snow |
| 2010/0211175 A1* | 8/2010 | Gomez-Llorens ......... 623/14.13 |

* cited by examiner

*Primary Examiner* — Charles A Marmor, II
*Assistant Examiner* — Carrie R Dorna
(74) *Attorney, Agent, or Firm* — Condo Roccia Koptiw LLP (57) ABSTRACT

A fluid transfer system for an inflatable sphincter prosthesis is disclosed. The implantable inflatable sphincter prosthesis may include a fluid transfer system and at least one inflatable cuff for occluding a body channel. The fluid transfer system may include an inflate pump, a deflate pump, and three one-way valves.

20 Claims, 5 Drawing Sheets

INFLATE PUMP          DEFLATE PUMP          CUFF

FIG. 1

INFLATE PUMP          DEFLATE PUMP          CUFF

FIG. 2

DEFLATE PUMP          INFLATE PUMP          CUFF

FLUID CONTROL SYSTEM FOR INFLATABLE SPHINCTER PROSTHESES

TECHNICAL FIELD

This disclosure relates generally to a fluid control system for implantable artificial inflatable urinary and anal sphincter prostheses.

BACKGROUND

In certain implantable prostheses, artificial urinary sphincters and artificial anal sphincters consisted of at least one inflatable cuff surrounding at least a portion of the urethra or anal canal and the cuff is inflated to provide continence or deflated to void, at least one fluid reservoir and a fluid transfer system consisting of at least one pump bulb and at least one valve. The fluid transfer system transfers fluid from the reservoir to inflate the cuff and returns fluid to the reservoir when the cuff is deflated.

SUMMARY

In certain implementations, a fluid transfer system for an inflatable sphincter prosthesis is described.

One embodiment is directed to an implantable sphincter prosthesis that includes a fluid transfer system and at least one inflatable cuff for occluding a body channel. The fluid transfer system includes an inflate pump having a first elastomeric pump bulb. The first elastomeric pump bulb is volitionally deformable to create a positive intraluminal pump pressure that forces fluid to be exhausted from the inflate pump. The fluid transfer system also includes a deflate pump having a second elastomeric pump bulb. The second elastomeric pump bulb is volitionally deformable to create a positive intraluminal pump pressure that forces fluid to be exhausted from the deflate pump. A first one-way valve is located between said inflate pump and said at least one inflatable cuff and has a first fluid flow through said first one-way valve directed from said inflate pump to said inflatable cuff. A second one-way valve is located between said inflatable cuff and said inflate pump and has a second fluid flow through said second one-way valve directed from said inflatable cuff to said inflate pump. The second one-way valve has a backpressure corresponding to a desired intraluminal pressure of the inflatable cuff in an inflated state. The first one-way valve has a backpressure greater than the backpressure of the second one-way valve. A third one-way valve is located between said inflatable cuff and said inflate pump and has a third fluid flow through said third one-way valve directed from said inflatable cuff to said inflate pump. The third one-way valve has at least substantially zero backpressure. The fluid transfer system enables fluid to flow from said inflate pump to said inflatable cuff when said inflate pump is volitionally deformed to provide patient continence. The fluid transfer system enables fluid to flow from said inflatable cuff to said deflate pump and said inflate pump upon activation of said deflate pump to permit patient voiding.

Another embodiment is directed to an implantable sphincter prosthesis that includes a fluid transfer system and at least one inflatable cuff for occluding a body channel. The fluid transfer system includes an inflate pump having a first elastomeric pump bulb. The first elastomeric pump bulb is volitionally deformable to create a positive intraluminal pump pressure that forces fluid to be exhausted from the inflate pump. Subsequent to volitional deformation, said first elastomeric pump bulb is incapable of imposing a negative intraluminal inflate pump pressure. The fluid transfer system also includes a deflate pump having a second elastomeric pump bulb. The second elastomeric pump bulb is volitionally deformable to create a positive intraluminal pump pressure that forces fluid to be exhausted from the deflate pump. Subsequent to volitional deformation, said second elastomeric pump bulb imposes a negative intraluminal deflate pump pressure to cause fluid to fill the deflate pump. A first one-way valve is located between said inflate pump and said at least one inflatable cuff and has a first fluid flow through said first one-way valve directed from said inflate pump to said inflatable cuff. A second one-way valve is located between said inflatable cuff and said inflate pump and has a second fluid flow through said second one-way valve directed from said inflatable cuff to said inflate pump. The second one-way valve has a backpressure corresponding to a desired intraluminal pressure of the inflatable cuff in an inflated state. The first one-way valve has a backpressure greater than the backpressure of the second one-way valve. A third one-way valve is located between said inflatable cuff and said deflate pump and has a third fluid flow through said third one-way valve directed from said inflatable cuff to said deflate pump. The third one-way valve has at least substantially zero backpressure. The fluid transfer system enables fluid to flow from said inflate pump to said inflatable cuff when said inflate pump is volitionally deformed to provide patient continence. The fluid transfer system enables fluid to flow from said inflatable cuff to said deflate pump and said inflate pump upon activation of said deflate pump to permit patient voiding.

One or more of the following advantages may be provided in certain implementations. First, a fluid transfer system can be provided that is easy to manufacture. Second, a fluid transfer system can be provided that allows the patient to volitionally evacuate fluid from at least one inflatable cuff to void. Third, a fluid transfer system can be provided that allows the patient to volitionally inflate at least one inflatable cuff immediately after voiding to provide instantaneous continence. Fourth, a fluid transfer system can be provided that maintains consistent intraluminal cuff pressure. Fifth, a fluid transfer system can be provided that does not require a switch to deactivate cuff inflation. Sixth, a fluid transfer system can be provided that does not require a pressurized reservoir with an established intraluminal pressure. A pressurized reservoir may elicit a contractible anatomical capsule that may impose unknown force on the pressurized reservoir, increasing the intraluminal pressure of the reservoir and inflatable cuff. Seventh, a fluid transfer system can be provided that incorporates a fluid reservoir for simplicity, so the entire prosthesis only requires a single tube connecting the fluid transfer system and fluid reservoir to the inflatable cuff. Eighth, a fluid transfer system can be provided that mitigates fluid uptake or loss within the prosthesis resulting from osmolality differential between the physiological solution used to operate a prosthesis and the physiology of the body, providing a consistent intraluminal cuff pressure. Ninth, a fluid transfer system can be provided having no resistance to flow from the inflatable cuff to the deflate pump bulb to minimize the thickness of the deflate pump bulb needed for pump bulb rebound and to facilitate a faster flow rate.

Tenth, a fluid transfer system can be provided that only requires a single tube to connect all of the components of a sphincter prosthesis, and that tube is to connect the fluid transfer system to an inflatable cuff.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

BRIEF DESCRIPTION OF THE DRAWINGS

FIG. 7-a is an exploded view of a valve forming part of the fluid transfer system of FIG. 7.

DETAILED DESCRIPTION

The inventive subject matter is described with specificity to meet statutory requirements. However, the description itself is not intended to limit the scope of this patent. Rather, it is contemplated that the claimed subject matter might also be embodied in other ways, to include different steps or combinations of steps similar to the ones described in this document, in conjunction with other present or future technologies.

Figure 1:
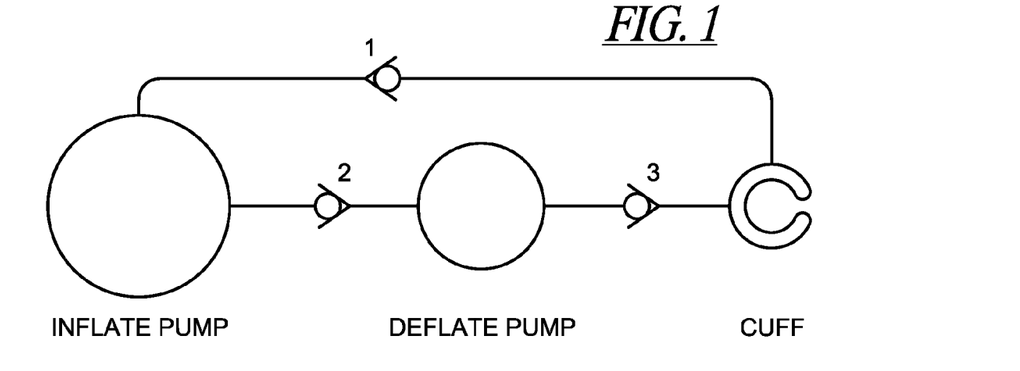
FIG. 1 is a schematic diagram depicting functional components of an implantable inflatable sphincter prosthesis.

FIG. 1 is a schematic diagram depicting functional components of an implantable inflatable sphincter prosthesis comprising a fluid transfer system and at least one inflatable cuff for occluding a body channel, such as a urethra. The fluid transfer system comprises an inflate pump, a deflate pump, and three one-way valves 1, 2, 3. FIG. 1 schematically depicts an inflate pump having a collapsible elastomeric pump bulb. The elastomeric pump bulb may be volitionally deformable to create a positive intraluminal pump pressure that may force fluid to be exhausted from the inflate pump. After volitional deformation, the elastomeric pump bulb may be incapable of imposing a negative intraluminal pump pressure.

FIG. 1 schematically depicts a deflate pump having an elastomeric pump bulb. The elastomeric pump bulb may be volitionally deformable to create a positive intraluminal pump pressure that may force fluid to be exhausted from the deflate pump. After volitional deformation, the elastomeric pump bulb may impose a negative intraluminal deflate pump pressure that may cause fluid to fill the deflate pump. A one-way valve 1 is depicted having a backpressure greater than a valve 2. In the example shown in FIG. 1, the valve 1 may be located between the inflate pump and the inflatable cuff with fluid flow through the valve 1 directed from the inflate pump to the inflatable cuff. A one-way valve 2 is depicted having a backpressure corresponding to the desired intraluminal pressure of the inflated cuff. The valve 2 may be located between the inflate pump and the inflatable cuff with fluid flow through the valve 2 directed from the inflatable cuff to the inflate pump. A one-way valve 3 is depicted having zero backpressure. The valve 3 may be located between the inflatable cuff and the deflate pump with fluid flow through the valve 3 directed from the inflatable cuff to the deflate pump. By way of example and not limitation, the one-way valve 3 can be implemented as an unbiased check valve as disclosed in U.S. patent application Ser. No. 13/467,024, filed May 8, 2012, the entire disclosure of which is hereby incorporated by reference. The fluid transfer system may enable fluid to flow from the inflate pump to the inflatable cuff when the inflate pump is volitionally deformed to provide patient continence and may enable fluid to flow from the inflatable cuff to the deflate pump and the inflate pump upon activation of the deflate pump to permit patient voiding.

Pressure applied to a body canal, such as a urethra, can occlude the canal to provide patient continence. However, the body canal associated with the artificial sphincter may undergo erosion. Some devices have been presented, and some sphincter configurations have been proposed, to accomplish patient continence with minimal erosion of the body canal. For example, a pressure regulating balloon (PRB) inflatable sphincter prosthesis may be used. Such sphincter prostheses may utilize an elastomeric balloon that may apply pressure to at least one inflatable cuff. Surgeons can choose from a range of PRB pressures.

In FIG. 1, the one-way valve 2 may have a backpressure corresponding to the desired intraluminal pressure of the inflated cuff. The valve 2 can be provided with a range of backpressure as disclosed in Table 1. It will be appreciated that the valve 2 can be provided with other backpressure values that are not disclosed in Table 1.

TABLE 1

| VALVE 2 BACKPRESSURE OPTIONS | |
|---|---|
| OPTION A | 45 cm $H_2O$ |
| OPTION B | 55 cm $H_2O$ |
| OPTION C | 65 cm $H_2O$ |
| OPTION D | 75 cm $H_2O$ |
| OPTION E | 85 cm $H_2O$ |

Figure 2:
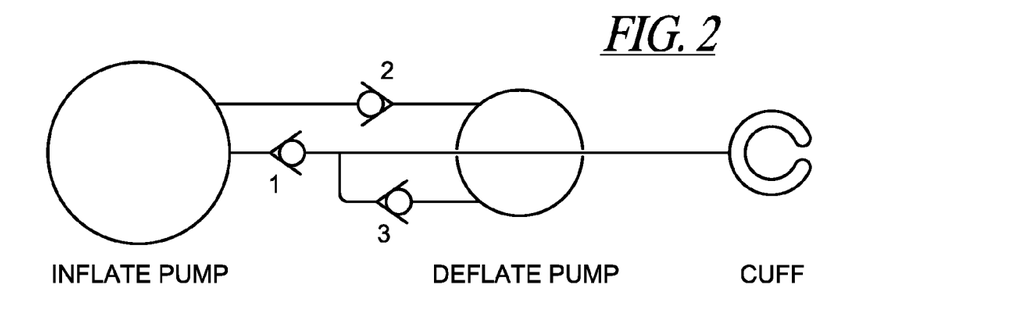
FIG. 2 is a schematic diagram depicting functional components of an implantable inflatable sphincter prosthesis with the inflate pump located distally from the inflatable cuff.

FIG. 2 is a schematic diagram depicting functional components of an implantable inflatable sphincter prosthesis with the inflate pump distal, e.g., most distal, from the inflatable cuff. The fluid transfer system may be an integral component comprising an inflate pump, a deflate pump and valve 1, valve 2, and valve 3.

Figure 3:
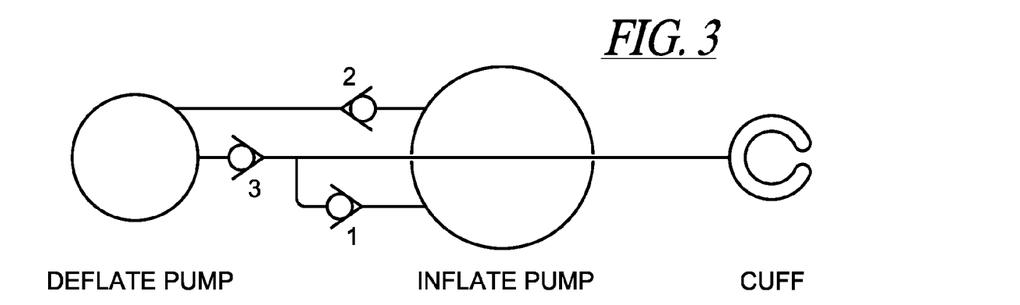
FIG. 3 is a schematic diagram depicting functional components of an implantable inflatable sphincter prosthesis with the deflate pump located distally from the inflatable cuff.

FIG. 3 is a schematic diagram depicting functional components of an implantable inflatable sphincter prosthesis with the deflate pump distal, e.g., most distal, from the inflatable cuff. The fluid transfer system may be an integral component comprising an inflate pump, a deflate pump and valve 1, valve 2 and valve 3.

FIG. 2 and FIG. 3 depict an implantable prosthesis having a single tube for fluid communication between device components. The single tube may connect the fluid transfer system and the inflatable cuff.

In FIGS. 1-3, the positioning of valve 2 and valve 3 may be interchanged while still maintaining the desired intraluminal cuff pressure. However, there may be a number of advantages to the valve locations depicted in FIGS. 1-3. For example, using the valve locations depicted in FIGS. 1-3 may realize an implantable prosthesis where there is little or no resistance to flow from the inflatable cuff to the deflate pump. As a result, the negative intraluminal deflate pump pressure involved in evacuating fluid from the inflatable cuff may be inconsequential. If valve 2 were located between the deflate pump and the inflatable cuff, the deflate pump may have to exert a negative intraluminal pressure greater than the backpressure of the valve 2 to open valve 2, potentially involving a stiffer deflate pump bulb. As another example, with valve 3 located between the inflatable cuff and the deflate pump, one-way valve 3 can include a vent feature that may allow fluid pressure to equilibrate between the deflate pump and the inflatable cuff. This pressure equilibration across valve 3 between the deflate pump and the inflation cuff may allow the deflate pump to function as a pressure reservoir for the inflation cuff to maintain the desired intraluminal cuff pressure. There are several ways to convert one-way valve 3 to include a vent feature. For example, the valve 3 valve seat could include one or more slight projections or one or more slight indentations to facilitate fluid migration across the valve seat if a pressure differential across the valve seat occurs. Similarly, the fluid port leading into valve 3 could have one or more projections or fins that project inward and that contact the ball or poppet to facilitate fluid migration across the valve seat if a pressure differential across the valve seat occurs. When the deflate pump is subjected to volitional deformation, higher intraluminal deflate pump pressure may prevent fluid migration across the valve seat. Even if fluid migration occurs across the valve seat during elevated intraluminal deflate pump pressure, it may be inconsequential to device performance.

Implantable inflatable sphincter prostheses may include artificial urinary sphincters for treatment of urinary incontinence and artificial anal sphincters for treatment of fecal incontinence. With inflatable sphincter prostheses, at least one inflatable cuff may partially or completely surround the urethra or anal canal. An example of a sphincter prosthesis having an inflatable cuff that may partially contact the urethra is a sling-type configuration where an inflatable cuff or member is supported on either side of the urethra with straps that are secured to bone or tissue.

Figure 4:
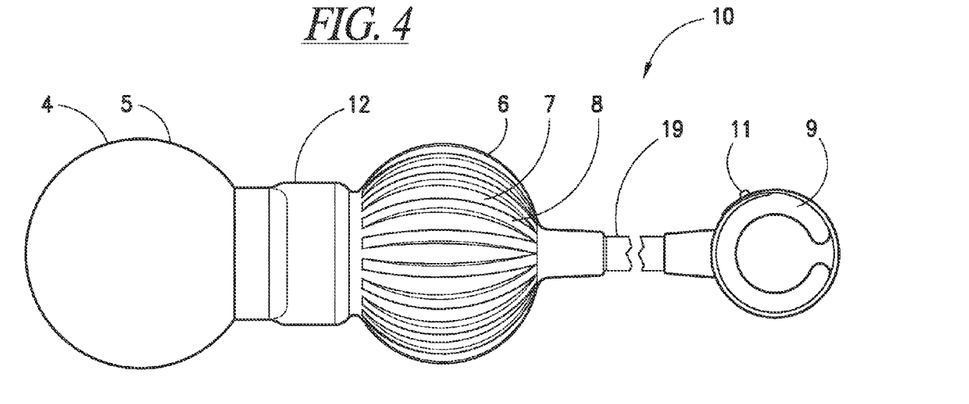
FIG. 4 illustrates an implantable inflatable sphincter prosthesis having the inflate pump located distally from the deflate pump and inflatable cuff.

FIG. 4 illustrates an implantable inflatable sphincter prosthesis 10 having an inflate pump 4 distal, e.g., most distal, to a deflate pump 6 and an inflatable cuff 9. The inflate pump 4 may include an inflate pump bulb 5. A valve body 12 containing one or more valves may be positioned between the inflate pump 4 and the deflate pump 6. The deflate pump 6 may have an elastomeric pump bulb 7 that may include longitudinal projections or ribs 8 that serve to enhance the gripping surface of the elastomeric pump bulb 7. The projections 8 may also function as stiffeners to provide greater pump bulb recovery or rebound subsequent to pump bulb deformation. In addition, the projections 8 may facilitate a thinner pump bulb wall that may afford greater fatigue resistance. The inflatable cuff 9 may be implemented as a type of inflatable cuff that surrounds a body channel and that may be connected to the fluid transfer system with tubing 19. An adjustable strap 11 may be affixed to the inflatable cuff 9 and may be used to fit the inflatable cuff 9 around a body channel and secure it to the body channel.

Figure 5:
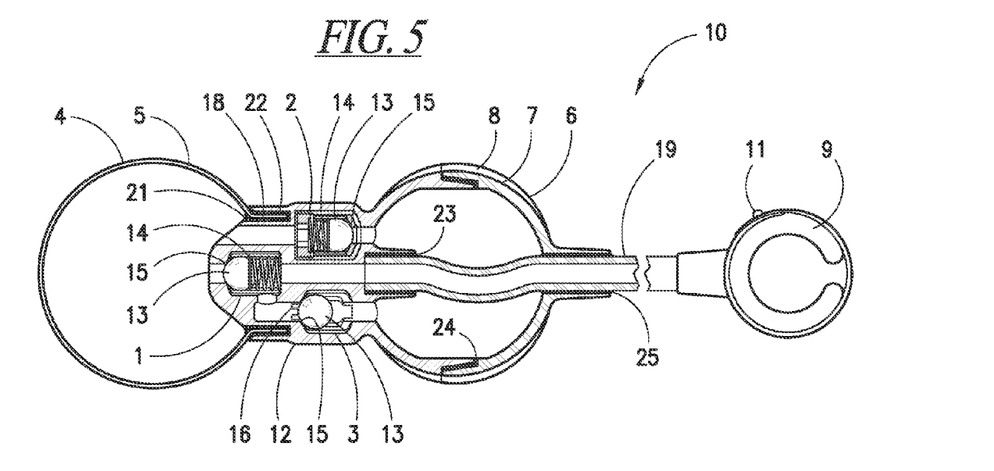
FIG. 5 is a sectional view of the fluid transfer system of the sphincter prosthesis depicted in FIG. 4.
Figure 5A:
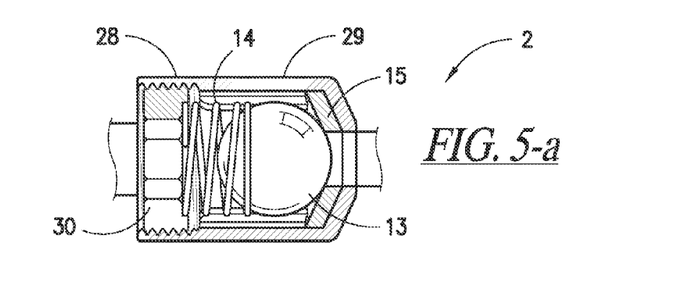
FIG. 5a is a sectional view of the fluid transfer system of the sphincter prosthesis depicted in FIG. 5.

FIG. 5 is a sectional view of the fluid transfer system of the sphincter prosthesis 10 depicted in FIG. 4. The inflate pump 4 may include an inflate pump bulb 5 having pump bulb neck 18. The pump bulb 5 and pump bulb neck 18 may be fabricated as a single component from an elastomer, such as silicone or polyurethane, with a wall thickness of approximately 0.015-inch. The valve body 12 may be molded from a silicone elastomer and may include a portion of the elastomeric deflate pump bulb 7. The tubing 19 may be fabricated from an elastomer, such as silicone, and may include a spiral reinforcement, such as a nylon filament, for greater kink resistance.

The pump bulb neck 18 may be used to secure the inflate pump bulb 5 to the valve body 12. An inner adhesive bond 21 between the interior of the pump bulb neck 18 and the valve body 12 and an outer adhesive bond 22 between the exterior of the pump bulb neck 18 may secure the pump bulb neck 18 to the valve body 12. An adhesive bond 23 may the secure tubing 19 to the valve body 12. An adhesive bond 24 may secure both pump bulb segments together. An adhesive bond 25 may secure the tubing 19 to the deflate pump bulb 7.

Figure 6:
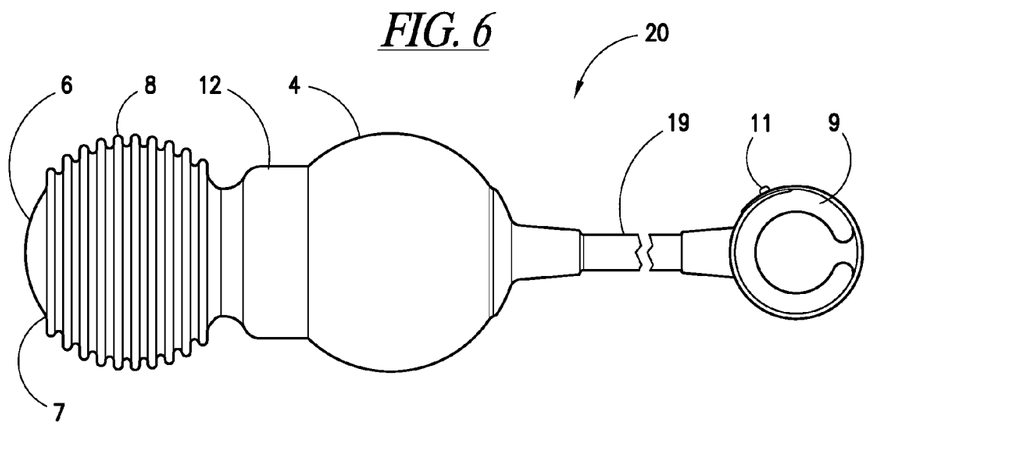
FIG. 6 illustrates an implantable inflatable sphincter prosthesis having the deflate pump located distally from the inflate pump and inflatable cuff.

FIG. 6 illustrates an implantable inflatable sphincter prosthesis 20 having a deflate pump 6 distal, e.g., most distal, to an inflate pump 4 and an inflatable cuff 9. A valve body 12 containing one or more valves may be positioned between inflate pump 4 and deflate pump 6. The deflate pump 6 may have an elastomeric pump bulb 7 that may include radial projections or ribs 8 that may serve to enhance the gripping surface of elastomeric pump bulb 7. The projections 8 may also function as stiffeners to provide greater pump bulb recovery or rebound subsequent to pump bulb deformation. The projections 8 may also facilitate a thinner pump bulb wall that affords greater fatigue resistance. The inflatable cuff 9 may surround a body channel and may be connected to the fluid transfer system with tubing 19. An adjustable strap 11 may be affixed to the inflatable cuff 9 and may be used to fit the inflatable cuff 9 around a body channel and to secure the inflatable cuff 9 to the body channel.

Figure 7:
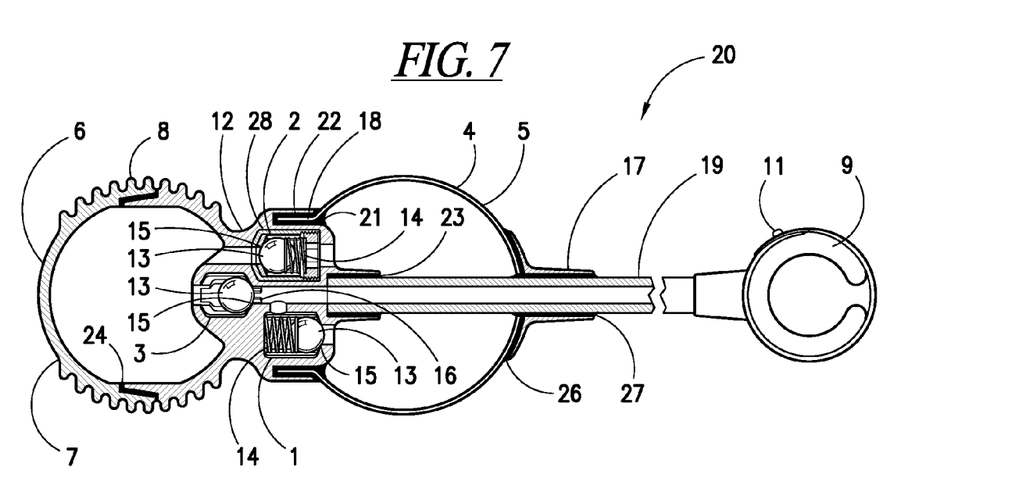
FIG. 7 is a sectional view of the fluid transfer system of the sphincter prosthesis depicted in FIG. 6.
Figure 7A:
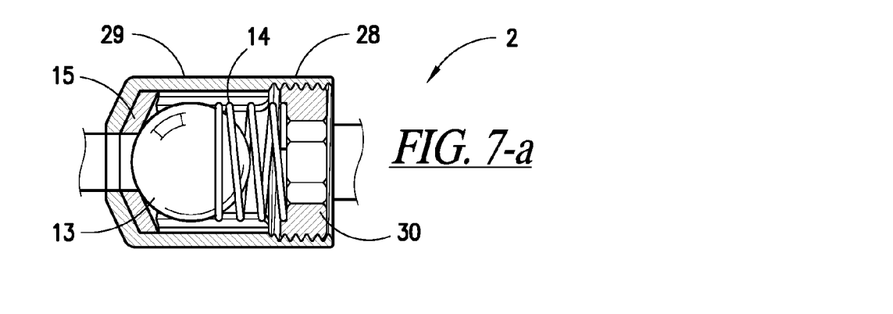

FIG. 7 is a sectional view of the fluid transfer system of the sphincter prosthesis 20 depicted in FIG. 6. An inflate pump 4 may include an inflate pump bulb 5 having a pump bulb neck 18. The pump bulb 5 and pump bulb neck 18 may be fabricated as a single component from an elastomer, such as silicone or polyurethane, with a wall thickness of approximately 0.015 inch. The valve body 12 may be molded from a silicone elastomer and may include a portion of elastomeric deflate pump bulb 7. The tubing 19 may be fabricated from an elastomer, such as silicone, and may include a spiral reinforcement, such as a nylon filament, for greater kink resistance.

An adhesive bond 24 may secure both pump bulb segments together. The pump bulb neck 18 may be used to secure the inflate pump bulb 5 to the valve body 12. An inner adhesive bond 21 between the interior of the pump bulb neck 18 and the valve body 12 and an outer adhesive bond 22 between the exterior of the pump bulb neck 18 may secure the pump bulb neck 18 to the valve body 12. An adhesive bond 23 may secure the tubing 19 to the valve body 12. An adhesive bond 26 may secure an tubing adapter 17 to the inflate pump bulb 5. An adhesive bond 27 may secure the tubing 19 inside of the tubing adapter 17.

In FIG. 5 and FIG. 7, valve 1 may be a one-way valve that may allow fluid transfer from the inflate pump 4 to the inflatable cuff 9. Valve 1 may include a valve seat 15, a ball or poppet 13, and a spring 14. Valve 1 may be configured to have a backpressure greater than valve 2, for example, within a range of 1.5 to 2.0 psi. Valve 2 may be a one-way valve that may allow fluid transfer from the inflatable cuff 9 into the inflate pump 4 via valve 3 and the deflate pump 6. Valve 2 may include a valve seat 15, a ball or poppet 13, and/or a spring 14. Valve 2 may be configured to have a backpressure corresponding to the desired intraluminal pressure of the inflated cuff and can be provided with a range of backpressure values as disclosed in Table 1. It will be appreciated that other backpressure values not disclosed in Table 1 may be used. Valve 3 may be a one-way valve that may allow fluid transfer from the inflatable cuff 9 to the deflate pump 6. Valve 3 may include a valve seat 15 and a ball or poppet 13. The fluid port leading into valve 3 may have fins 16 that project inward and contact ball 13 to facilitate fluid migration across valve seat 15 if a pressure differential across valve seat 15 occurs. When deflate pump 6 is subjected to volitional deformation, higher intraluminal pressure in deflate pump 6 may prevent fluid migration across valve seat 15. Even if fluid migration occurs across valve seat 15 during elevated intraluminal deflate pump pressure, it may be inconsequential to device performance. Valve seats 15 may be part of the elastomeric valve body 12, and may be formed from silicone elastomer such as Nusil Technology MED4755. Ball 13 may also be a poppet and can be fabricated from a metal such as MP35N nickel-cobalt alloy. Alternately, ball or poppet 13 could be fabricated from a plastic such as polypropylene or nylon, if it is not in contact with a metal spring. Spring 14 can be coiled from a metal wire such as MP35N. Alternately, spring 14 could be fabricated from a plastic, such as Udel P1700 polysulfone, that exhibits low compression creep. Adhesive bonds 21, 22, 23, 24, 25, 26, and 27 may comprise an elastomeric adhesive such as room temperature vulcanized (RTV) silicone adhesive. The deflate pump bulb 7 of deflate pump 6 may be fabricated from a silicone elastomer, such as Nusil Technology MED4755. The inflate pump bulb 5 of inflate pump 4 can be fabricated, for example, from either a silicone or polyurethane elastomer.

In FIG. 5 and FIG. 7, one-way valve 2 is a cartridge valve 28. FIG. 5-a is an exploded view of valve 2 of FIG. 5. FIG. 7-a is an exploded view of valve 2 of FIG. 7. FIG. 5-a and FIG. 7-a depict a cartridge valve 28 comprising a cartridge 29 having internal threads, a ball or poppet valve 13, a valve seat 15, a compression spring 14, and a hex set screw 30 with a through hold that may serve as a fluid port. The hex set screw 30 may be factory adjusted to provide the required spring compression to create a desired backpressure for valve 2. The cartridge 29 may be fabricated from a plastic, such as polysulfone, or a metal, such as titanium or MP35N nickel-cobalt alloy. Likewise, the compression spring 14 may be fabricated as a coiled metal wire or molded plastic spring. The purpose of cartridge valve 28 is twofold. First, with a low-pressure, e.g., less than 100 centimeters of water backpressure, valve 2, it may be difficult to target precise valve backpressure, so the hex set screw 30 can be used to compensate for spring 14 and valve seat 15 variations. The cartridge valve 28 also accommodates valve seat 15 of a desired material composition and hardness that may be different than the elastomer used for valve body 12. Secondly, low backpressure valves in general may be susceptible to valve opening from distortion and mechanical shock because the spring is not applying much force to keep the valve closed. The cartridge 29 may prevent distortion of valve seat 15 and spring 14 and may facilitate incorporation of valve seat 15 with desired anti-shock characteristics. These characteristics might include a low durometer elastomer or an elastomer with a low coefficient of friction.

Figure 5B:
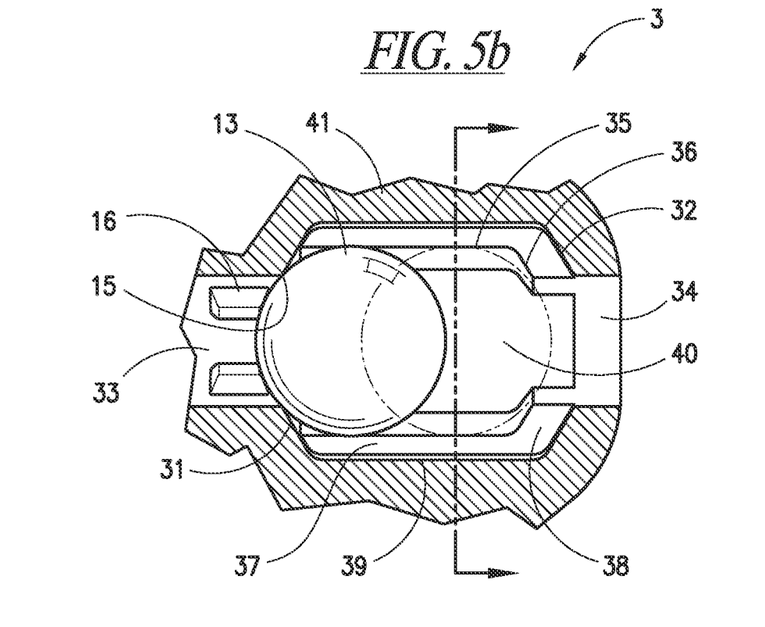
FIG. 5b is an exploded view of a valve forming part of the fluid transfer system of FIG. 5.
Figure 5C:
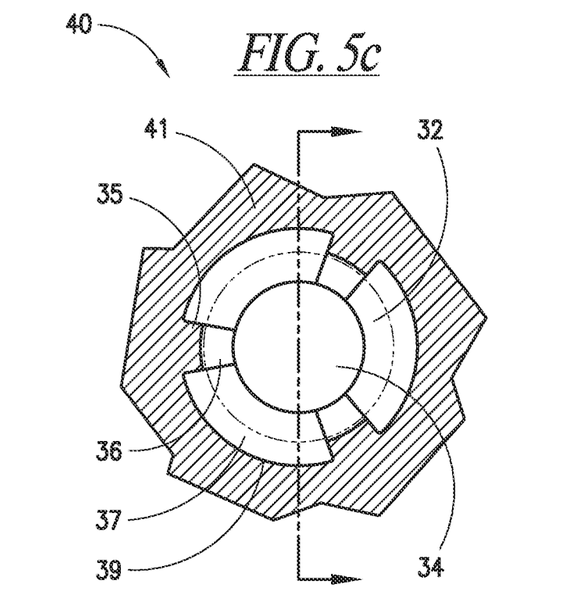
FIG. 5c is a sectional view of a chamber of the unbiased valve shown in FIG. 5b.
Figure 8:
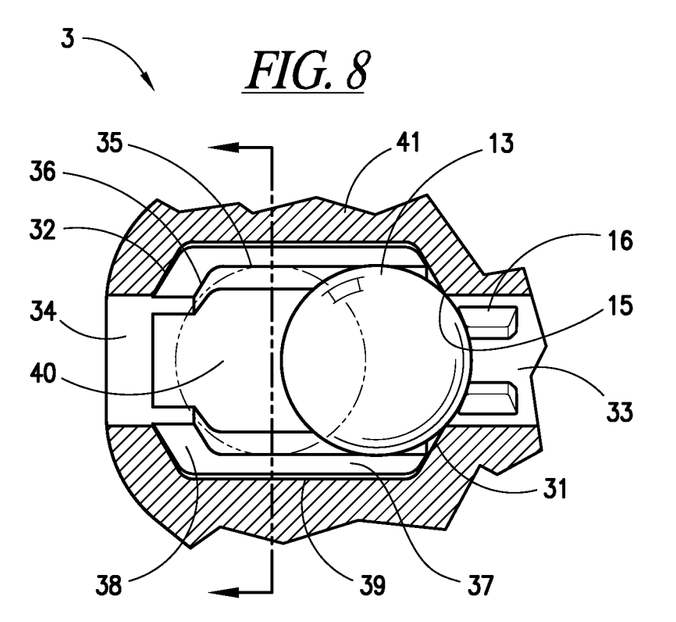
FIG. 8 is an exploded view of an unbiased valve forming part of the fluid transfer system of FIG. 7.
Figure 8A:
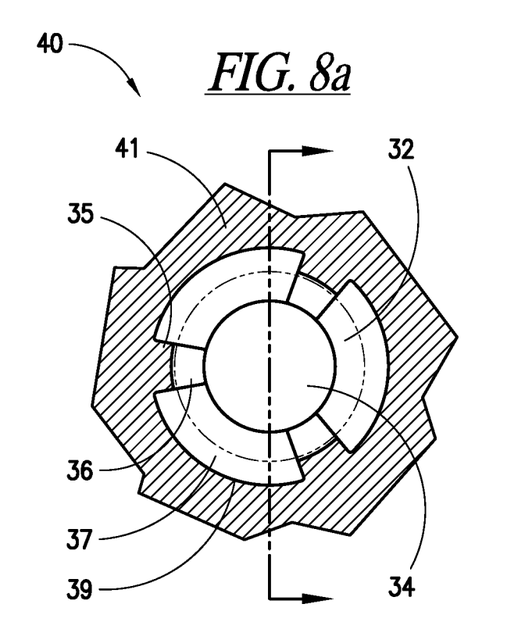
FIG. 8a is a sectional view of a chamber of the unbiased valve shown in FIG. 8.

FIG. 5b depicts an unbiased check valve assembly of the type depicted for the unbiased valve 3 assembly in FIG. 5. FIG. 8 depicts an unbiased check valve assembly of the type depicted for the unbiased valve 3 assembly in FIG. 7. FIG. 5c is a cross-sectional view of a wall of valve chamber 40 taken from FIG. 5b. FIG. 8a is a cross-sectional view a wall of valve chamber 40 taken from FIG. 8. FIG. 5c and FIG. 8 depict a chamber end 32 with an exit port 34. The unbiased check valve 3 assembly may be configured with the valve chamber 40 having an entry port 33 on a valve chamber end 31 and an exit port 34 on a valve chamber end 32 opposite the entry port 33 and a valve chamber wall interior surface 39 between chamber ends 31 and 32. The valve seat 15 may be formed at the junction where the chamber end 31 and the entry port 33 connect. Unbiased check valve 3 assembly may have an elastomeric chamber wall 41 so valve seat 15 may be molded integral with the chamber wall 41. The surface of the chamber end 32 containing the exit port 34 may be irregular to prevent the valve 13 from seating against the exit port 34, allowing fluid to flow around the valve 13 and through the exit port 34. Radial ribs 36 emanating from the chamber end 32 may provide an irregular surface to permit fluid flow around valve 13 in the radial flow channels 38 between the radial ribs 36 and the chamber end 32. Axial ribs 35 emanating from the valve chamber wall interior surface 39 may keep valve 13 in the center of the valve chamber 40. Axial flow channels 37 between the axial ribs 35 and the interior surface 39 may allow fluid flow around the valve 13. In valve 3, the valve chamber 40 may cooperate with a ball or poppet valve component 13 having a specific gravity substantially equivalent to the physiological fluid used to operate the prosthesis, to provide an unbiased valve. The valve component 13 may be fabricated from a plastic, such as polypropylene, having a specific gravity substantially equivalent to the physiological fluid used to operate the prosthesis. Because artificial inflatable sphincter prostheses may be implanted entirely within the human body, the materials selected for the components should be biocompatible and biostable for long term use in vivo.

Operation of Sphincter Prosthesis with Fluid Transfer System

Activation of an inflatable sphincter prosthesis with a fluid transfer system disclosed herein may be patient-friendly. To operate the prosthesis, the patient may squeeze the inflate pump 4 once to inflate the inflatable cuff 9 and initiate continence. The patient may squeeze the deflate pump 6 one or more times to deflate inflatable cuff 9 to facilitate voiding. Table 2 provides an example sequence of operations detailing valve characteristics and functions.

TABLE 2

SEQUENCE OF OPERATIONS

| Valve Number | Valve Backpressure | CUFF INFLATION | | CUFF DEFLATION | |
|---|---|---|---|---|---|
| | | Squeeze Inflate Pump | Release Inflate Pump | Squeeze Deflate Pump | Release Deflate Pump |
| 1 | 1.5-2.0 psi | OPENS | CLOSES | CLOSED | CLOSED |
| 2 | 45-85 cm H₂O | CLOSED | OPENS | OPENS | CLOSES |
| 3 | 0 psi | OPENS | OPENS | CLOSES | OPENS |

Notes:
1. Valves may open when pressure exceeds valve backpressure.
2. Valve 3 may include a vent for equilibration of pressure differential between deflate valve and inflatable cuff.

Various modifications and additions can be made to the exemplary embodiments discussed without departing from the scope of the present disclosure. While the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. An implantable sphincter prosthesis comprising a fluid transfer system and an inflatable cuff for occluding a body channel, said fluid transfer system comprising:
- an inflate pump having a first elastomeric pump bulb, said first elastomeric pump bulb being volitionally deformable to create a positive intraluminal pump pressure that forces fluid to be exhausted from the inflate pump;
- a deflate pump having a second elastomeric pump bulb, said second elastomeric pump bulb being volitionally deformable to create a positive intraluminal pump pressure that forces fluid to be exhausted from the deflate pump;
- a first one-way valve located between said inflate pump and said inflatable cuff with a first fluid flow through said first one-way valve directed from said inflate pump to said inflatable cuff;
- a second one-way valve located between said inflatable cuff and said inflate pump with a second fluid flow through said second one-way valve directed from said inflatable cuff to said inflate pump, the second one-way valve having a backpressure corresponding to a desired intraluminal pressure of the inflatable cuff in an inflated state, the first one-way valve having a backpressure greater than the backpressure of the second one-way valve; and
- a third one-way valve located between said inflatable cuff and said inflate pump and having a third fluid flow through said third one-way valve directed from said inflatable cuff to said inflate pump, the third one-way valve having at least substantially zero backpressure,
- wherein said fluid transfer system enables fluid to flow from said inflate pump to said inflatable cuff when said inflate pump is volitionally deformed to provide patient continence, and wherein volitional deformation of said second elastomeric pump bulb imposes a negative intraluminal deflate pump pressure that enables fluid to flow from said inflatable cuff to said deflate pump and said inflate pump upon activation of said deflate pump to permit patient voiding.

2. The implantable sphincter prosthesis of claim 1, wherein, subsequent to volitional deformation, said first elastomeric pump bulb is incapable of imposing a negative intraluminal inflate pump pressure.

3. The implantable sphincter prosthesis of claim 1, wherein, subsequent to volitional deformation, said second elastomeric pump bulb imposes a negative intraluminal deflate pump pressure to cause fluid to fill the deflate pump.

4. The implantable sphincter prosthesis of claim 1, wherein said second one-way valve comprises a cartridge valve comprising a cartridge having internal threads, a ball or poppet valve component, a valve seat, a compression spring, and a hex set screw with a through hole serving as a fluid port.

5. The implantable sphincter prosthesis of claim 4, wherein said hex set screw is factory adjusted to provide a spring compression to create a desired backpressure of the second one-way valve.

6. The implantable sphincter prosthesis of claim 1, wherein said second one-way valve has a backpressure in a range of 45 cm $H_2O$ to 85 cm $H_2O$.

7. The implantable sphincter prosthesis of claim 1, wherein said inflate pump is integral with said deflate pump and at least one of the first one-way valve, the second one-way valve, and the third one-way valve.

8. The implantable sphincter prosthesis of claim 1, further comprising a tube in fluid communication with and connecting said fluid transfer system and said inflatable cuff.

9. The implantable sphincter prosthesis of claim 1, wherein said inflate pump is located distally from said deflate pump and said inflatable cuff.

10. The implantable sphincter prosthesis of claim 1, wherein said deflate pump is located distally from said inflate pump and said inflatable cuff.

11. The implantable sphincter prosthesis of claim 1, wherein said implantable prosthesis comprises one of an artificial urinary sphincter for treatment of urinary incontinence and an artificial anal sphincter for treatment of fecal incontinence.

12. The implantable sphincter prosthesis of claim 1, wherein said inflatable cuff is configured to completely encircle a urethra or an anal canal.

13. The implantable sphincter prosthesis of claim 1, wherein said inflatable cuff is configured to partially contact a urethra or an anal canal.

14. The implantable sphincter prosthesis of claim 13, further comprising a sling arrangement configured to support said inflatable cuff.

15. The implantable sphincter prosthesis of claim 1, further comprising a valve body positioned between said inflate pump and said deflate pump and containing one or more valves.

16. The implantable sphincter prosthesis of claim 1, wherein said deflate pump comprising an elastomeric pump bulb having projections formed thereon.

17. An implantable sphincter prosthesis comprising a fluid transfer system and an inflatable cuff for occluding a body channel, said fluid transfer system comprising:
- an inflate pump having a first elastomeric pump bulb, said first elastomeric pump bulb being volitionally deformable to create positive intraluminal pump pressure that forces fluid to be exhausted from the inflate pump, wherein, subsequent to volitional deformation, said first elastomeric pump bulb is incapable of imposing a negative intraluminal inflate pump pressure;
- a deflate pump having a second elastomeric pump bulb, said second elastomeric pump bulb being volitionally deformable to create a positive intraluminal pump pressure that forces fluid to be exhausted from the deflate pump, wherein, subsequent to volitional deformation, said second elastomeric pump bulb imposes a negative intraluminal deflate pump pressure to cause fluid to fill the deflate pump;
- a first one-way valve located between said inflate pump and said inflatable cuff with a first fluid flow through said first one-way valve directed from said inflate pump to said inflatable cuff;
- a second one-way valve located between said deflate pump and said inflate pump with a second fluid flow through said second one-way valve directed from said deflate pump to said inflate pump, the second one-way valve having a backpressure corresponding to a desired intraluminal pressure of the inflatable cuff in an inflated state, the first one-way valve having a backpressure greater than the backpressure of the second one-way valve; and
- a third one-way valve located between said inflatable cuff and said deflate pump with a third fluid flow through said third one-way valve directed from said inflatable cuff to said deflate pump, the third one-way valve having at least substantially zero backpressure,
- wherein said fluid transfer system enables fluid to flow from said inflate pump to said inflatable cuff when said inflate pump is volitionally deformed to provide patient continence, and wherein said third fluid flow enables fluid to flow from said inflatable cuff to said deflate pump and said inflate pump upon activation of said deflate pump to permit patient voiding.

18. The implantable sphincter prosthesis of claim 17, wherein the third one-way valve includes a vent feature that allows fluid pressure to equilibrate between said deflate pump and said inflatable cuff to cause said deflate pump to function as a pressure reservoir for said inflation cuff to maintain the desired intraluminal cuff pressure.

19. The implantable sphincter prosthesis of claim 18, wherein said vent feature comprises at least one of a projection, an indentation of the valve seat, or a fin within the fluid port leading into the third one-way valve.

20. The implantable sphincter prosthesis of claim 17, wherein the third one-way valve comprises an unbiased check valve utilizing a ball or poppet component having a specific gravity substantially equivalent to the specific gravity of the fluid used to fill the device.

\* \* \* \* \*